(12) United States Patent
Fougeroux et al.

(10) Patent No.: US 9,303,446 B2
(45) Date of Patent: Apr. 5, 2016

(54) DETECTION GATE

(75) Inventors: Nicolas Fougeroux, Paris (FR); Olivier Touret, Paris (FR)

(73) Assignee: MORPHO, Paris (FR)

( * ) Notice: Subject to any disclaimer, the term of this patent is extended or adjusted under 35 U.S.C. 154(b) by 662 days.

(21) Appl. No.: 13/513,319

(22) PCT Filed: Nov. 29, 2010

(86) PCT No.: PCT/EP2010/068442
§ 371 (c)(1),
(2), (4) Date: Sep. 18, 2012

(87) PCT Pub. No.: WO2011/067215
PCT Pub. Date: Jun. 9, 2011

(65) Prior Publication Data
US 2013/0000385 A1     Jan. 3, 2013

(30) Foreign Application Priority Data

Dec. 2, 2009  (FR) ...................................... 09 58578

(51) Int. Cl.
| *G01N 1/24* | (2006.01) |
| *E06B 5/00* | (2006.01) |
| *G01N 1/02* | (2006.01) |

(52) U.S. Cl.
CPC .. *E06B 5/00* (2013.01); *G01N 1/24* (2013.01); *G01N 2001/024* (2013.01)

(58) Field of Classification Search
CPC ............... G01N 2001/024; G01N 2001/2223; G01N 2001/022; G01N 2001/025; G01N 2001/2276; G01N 2001/245; G01N 2001/028; G01N 21/3504; G01N 21/359; G01N 21/39; G01N 33/497
See application file for complete search history.

(56) References Cited

U.S. PATENT DOCUMENTS

| 3,190,207 | A | * | 6/1965 | Weisz ........................... 454/191 |
| 3,588,496 | A | * | 6/1971 | Snowman ...................... 250/343 |
| 4,045,997 | A | * | 9/1977 | Showalter et al. .............. 73/23.2 |
| 4,202,200 | A | * | 5/1980 | Ellson .......................... 73/31.05 |
| 4,896,547 | A | * | 1/1990 | Arney et al. ................ 73/863.81 |
| 4,909,089 | A | * | 3/1990 | Achter et al. ............... 73/863.11 |
| 4,964,309 | A | * | 10/1990 | Jenkins ....................... 73/864.81 |
| D313,766 | S | * | 1/1991 | Arney et al. .............. D10/104.1 |
| 4,987,767 | A | * | 1/1991 | Corrigan et al. ............. 73/23.36 |
| 5,668,342 | A | * | 9/1997 | Discher ............................ 86/50 |
| 5,753,832 | A | * | 5/1998 | Bromberg et al. .......... 73/864.81 |
| 5,760,314 | A | * | 6/1998 | Bromberg et al. .......... 73/863.21 |
| 5,894,130 | A | * | 4/1999 | Bach ............................. 250/436 |
| 5,915,268 | A | * | 6/1999 | Linker et al. ................... 73/23.2 |

(Continued)

*Primary Examiner* — David A Rogers
(74) *Attorney, Agent, or Firm* — Bachman & LaPointe, P.C.

(57) ABSTRACT

A detection gate for detecting substances carried by an individual or an object, has two lateral uprights facing one another and defining a passage there between for the individual or the object, a blowing device installed in a blowing chamber in one of the uprights which are adapted to exhaust the air contained in the blowing chamber towards the other upright, an exhaust device installed in an exhaust chamber in the other upright, which are suitable for exhausting the air thus blown, a detection device arranged upstream from the passage and adapted to detect the presence of the substances in the air thus blown, and a transfer line which, via one of the ends thereof, leads into the blowing chamber and, via the other end thereof, into the exhaust chamber, the blowing device and the exhaust device being such that a single volume of air has time to pass through the passage at least twice during the time that individual or the object is present in the passage.

7 Claims, 2 Drawing Sheets

(56) References Cited

U.S. PATENT DOCUMENTS

| | | | |
|---|---|---|---|
| 5,942,699 A * | 8/1999 | Ornath et al. | 73/863.21 |
| 6,073,499 A * | 6/2000 | Settles | 73/864.81 |
| 6,334,365 B1 * | 1/2002 | Linker et al. | 73/864.81 |
| 6,366,203 B1 * | 4/2002 | Burns | 340/551 |
| 6,375,697 B2 * | 4/2002 | Davies | 55/340 |
| 6,610,977 B2 * | 8/2003 | Megerle | 250/287 |
| 6,708,572 B2 * | 3/2004 | Jenkins et al. | 73/864.33 |
| 6,790,249 B2 * | 9/2004 | Davies | 55/340 |
| 7,023,339 B2 * | 4/2006 | Stomski | 340/540 |
| 7,136,513 B2 * | 11/2006 | Waehner et al. | 382/118 |
| 7,141,786 B2 * | 11/2006 | McGann et al. | 250/287 |
| 7,180,441 B2 * | 2/2007 | Rowe et al. | 342/22 |
| 7,357,043 B2 * | 4/2008 | Cumming et al. | 73/864.33 |
| 7,594,422 B2 * | 9/2009 | Perry et al. | 73/1.02 |
| 7,666,356 B2 * | 2/2010 | O'Donnell et al. | 422/82.05 |
| 7,721,588 B2 * | 5/2010 | Perry et al. | 73/28.01 |
| 7,913,540 B2 * | 3/2011 | Brasfield | 73/23.34 |
| 7,942,033 B2 * | 5/2011 | Jenkins | 73/31.01 |
| 8,448,495 B2 * | 5/2013 | Breviere et al. | 73/31.05 |
| 8,671,737 B2 * | 3/2014 | Brasfield | 73/23.34 |
| 2001/0049926 A1 | 12/2001 | Davies | |
| 2003/0134427 A1 * | 7/2003 | Roller et al. | 436/171 |
| 2005/0057354 A1 * | 3/2005 | Jenkins et al. | 340/522 |
| 2006/0081073 A1 * | 4/2006 | Vandrish et al. | 73/864.33 |
| 2006/0243902 A1 | 11/2006 | Altes Royo | |
| 2007/0081162 A1 * | 4/2007 | Roller et al. | 356/437 |
| 2007/0086925 A1 | 4/2007 | O'Donnell et al. | |
| 2009/0044641 A1 * | 2/2009 | Konduri et al. | 73/863.11 |

* cited by examiner

DETECTION GATE

BACKGROUND

The present invention concerns a detection gate for detecting substances, for example drugs, explosives, etc. The present invention also concerns a detection method implemented in such a detection gate.

A detection gate for detecting substances of the drugs, explosives, etc. type is generally installed in sensitive places (airports, railway stations, etc.) to detect whether individuals or objects (luggage) have been in contact with such substances.

A detection gate of the prior art is known that comprises a frame having two lateral uprights facing each other and which define between them a passage for an individual or an object, and a device for collecting substances transported by the ambient air that is located at the top of the two lateral uprights in order to connect them.

Each lateral upright comprises a plurality of air ejection nozzles, each being oriented towards the individual in the passage in order, when an individual passes through the gate, to eject air towards the said individual in order to detach and entrain the particles that are embedded in his garments.

The collection device comprises an introduction window that is situated above the passage.

The particles pulled away during the ejection of air are entrained towards the said introduction window and are thus conducted to a detector.

The detector is able to recognise, among the particles thus pulled away, particles of illicit substances, such as drugs, explosives, etc.

When the detector detects one of these particles, it emits an alarm signal in order to warn a person in the monitoring service so as to permit any actions for dealing with this alarm.

Such a detection gate is not entirely satisfactory since it is based on a principle of isolated collection of solid particles of the substances related to the isolated emission of air jets by the nozzles. However, the signal thus obtained, in an isolated manner, intended for the detector, may prove to be insufficient in certain operational situations. Individuals carrying substances to be detected may then defeat the detection gate.

SUMMARY OF THE INVENTION

One object of the present invention is to propose a detection gate that does not have the drawbacks of the prior art and in particular affords a better detection of substances.

To this end, a detection gate intended to detect substances carried by an individual or an object is proposed, the detection gate comprising:
  two lateral uprights facing each other and defining between them a passage for the said individual or the said object,
  blowing means installed in a blowing chamber that one of the uprights has, and which are adapted to blow the air contained in the said blowing chamber towards the other upright,
  exhaust means installed in an exhaust chamber that the other upright has, and which are able to suck in the air thus blown,
  a detection device disposed downstream from the passage and able to detect the presence of the said substances in the air thus blown, and
  a transfer pipe emerging through one of its ends in the blowing chamber and through its other end in the exhaust chamber, the blowing means and the exhaust means being such that the same volume of air has the time to travel across the passage at least twice before the said individual or the said object passes through the said passage.

Advantageously, the blowing means comprise a plurality of fans distributed over the height of the upright.

Advantageously, at least one of the fans is arranged opposite the area where the feet of the individual pass.

Advantageously, the transfer pipe has a discharge flap able to move between a closed position and an open position.

Advantageously, the detection gate comprises a sterilisation device intended to sterilise the air flow circulating between the exhaust means and the blowing means.

Advantageously, the detection gate comprises a holding device intended to prevent the individual leaving the said detection gate.

The invention also proposes a method for detecting substances carried by an individual or object and implemented by means of a detection gate according to one of the above variants, the said detection method comprising:
  a blowing step during which a volume of air in the blowing chamber is blown by the blowing means towards the exhaust means,
  an exhaust step during which the said volume of air thus blown is exhausted by the exhaust means in the exhaust chamber,
  a detection step during which the detection device detects whether at least one of the said substances is present in the said volume of air thus blown,
  a transfer step during which the air in the exhaust chamber is transferred to the blowing chamber through the transfer pipe, and
  a step of looping back onto the blowing step, the blowing means and the exhaust means being such that the same volume of air has the time to make the blowing step and exhaust step twice before the said individual or the said object passes through the said passage.

Advantageously, when the detection gate comprises a sterilisation device, it comprises a sterilisation step between the detection step and the blowing step.

BRIEF DESCRIPTION OF THE DRAWINGS

The features of the invention mentioned above, as well as others, will emerge more clearly from a reading of the following description of an example embodiment, the said description being given in relation to the accompanying drawings, among which.

DETAILED DESCRIPTION OF THE PREFERRED EMBODIMENT(S)

Figure 1:
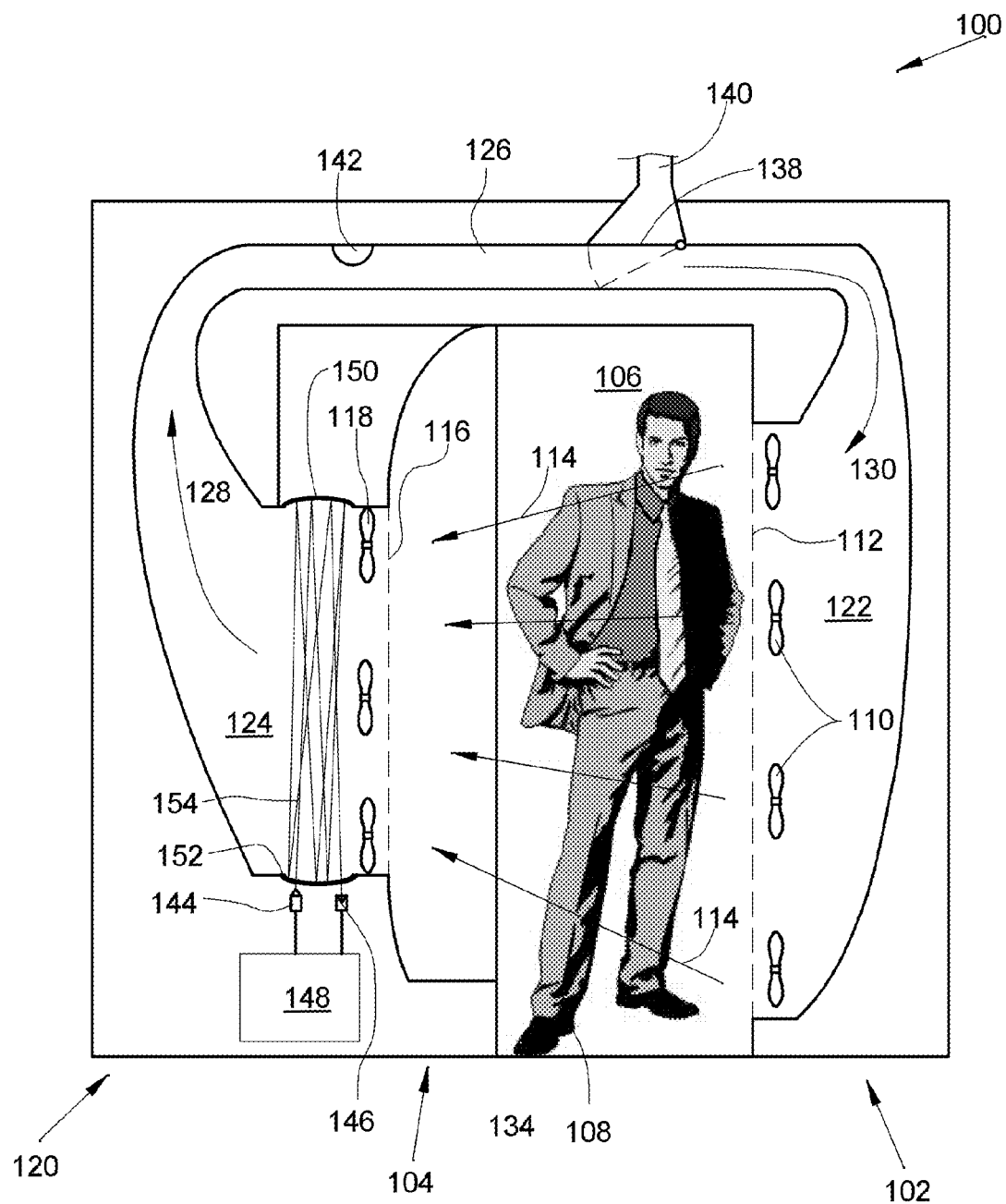
FIG. 1 shows a schematic view in section of a detection gate according to the invention.

In the following description, the terms relating to a position refer to a detection gate in operation, that is to say as shown in FIG. 1.

FIG. 1 shows a detection gate 100 according to the invention intended to detect substances carried by an individual 108 or an object.

The detection gate 100 comprises two lateral uprights 102 and 104 that face each other and define between them a passage 106 for the individual 108 or the object.

One of the uprights, here the upright 102, comprises a blowing chamber 122 delimited by a ventilated blowing wall 112 and in which blowing means 110 are installed, arranged behind the said ventilated wall 102 with respect to the passage 106. The blowing means 110 are able to blow the air contained in the blowing chamber 122 in the direction of the other upright 104, making this air pass through the passage 106.

The arrows 114 show the air flows between the two uprights 102 and 104.

The blowing means 110 consist for example here of a plurality of fans. The fans are distributed over the height of the upright 102 and each has a propeller, the rotation axis of which is here horizontal and perpendicular to the direction of movement of the individual 108 in the passage 106 and a motor (not shown) intended to rotate the propeller about its rotation axis.

The rotation axis of each propeller may be slightly inclined with respect to the horizontal.

The blowing direction 114 is here roughly perpendicular to the direction of travel of the individual 108.

In particular, one of the fans 110 is arranged opposite the area where the feet of the individual 108 pass, since the feet constitute a preferential area for transporting the substances sought.

The other upright, here the upright 104, comprises an exhaust chamber 124 delimited by a ventilated exhaust wall 116 in which exhaust means 118 are installed, arranged behind the said ventilated exhaust wall 116 with respect to the passage 106. The exhaust means 118 are able to exhaust the air that is blown from the upright 102 by the blowing means 110.

The exhaust means 118 consist here of a plurality of fans. The fans are distributed over the height of the upright 104 and each comprises a propeller the rotation axis of which is here horizontal and perpendicular to the direction of travel of the individual 108 through the passage 106 and a motor (not shown) intended to rotate the propeller around the rotation axis thereof.

Each chamber 122, 124 emerges in the passage 106 through the corresponding ventilated wall 112, 116.

The detection gate 100 also comprises, downstream from the passage 106 with respect to the direction of movement of the blown air flow (114) in the passage 106, and more particularly downstream from the exhaust means 118, a detection device 120. The detection device 120 is able to detect the presence of the substances (drugs, explosives, etc.) in the air blown by the blowing means 110 and to warn the responsible person so that the measures provided for in the case of a positive detection are implemented.

The detection gate 100 also comprises a transfer pipe 126 that emerges through one of the ends thereof in the blowing chamber 122 and through the other end thereof in the exhaust chamber 124.

The air that is in the exhaust chamber 124 is thus transferred into the transfer pipe 126 (arrow 128) and then into the blowing chamber 122 (arrow 130), where it is blown in the direction of the exhaust chamber 124.

The installation of the transfer pipe 124 generates an air flow (114, 128, 130) the majority or the volume of which circulates in closed circuit.

In the context of the invention, the air flows 114 are not isolated air jets but a continuous flow that best surrounds the individual 108 in order to capture and entrain the particles and vapours that surround him. This continuous flow, in so far as the performance of the detector in terms of detection time so allows, affords an analysis "on the fly" of the individual, without the obligation to stop him in the passage, as required by the prior art.

In addition, the speed of the air flow 114 is such that the same volume of air has the time to pass through the passage 106 at least twice during the presence of the individual 108 in the detection gate 100.

In other words, the blowing means 110 and the exhaust means 118 are adapted so that the same volume of air has the time to pass through the passage 106 at least twice while the individual 108 is present in the detection gate 100.

Thus, if the individual 108 is carrying substances to be detected, the fact that the same volume of air passes through the passage 108 twice, and therefore passes twice over the source of substance to be detected, increases the number of molecules of these substances since this same air has the opportunity, a second time, to entrain substances to be detected towards the detector. The concentration of these molecules of substances to be detected is then increased, which facilitates detection thereof by the detection device 120.

The dimensions of the detection gate 100 and the speeds of rotation of the propellers 110, 118 are chosen firstly so that the air that is blown by the blowing means 110 is almost entirely captured by the exhaust means 118 and secondly so that the air that is exhausted by the exhaust means 118 comes practically exclusively from the air blown by the blowing means 110.

In a particular embodiment, the width of the passage 106 is around 80 cm, the height of the passage is around 210 cm and the speed of the air flow in the passage 106 is around 3 m/s. The length of the path that the air must travel between the ventilated exhaust wall 116 and the ventilated blowing wall 112, through the transfer pipe 126, is around 4 m.

The depth of the detection gate 100, that is to say the distance that the individual 108 must travel between the two uprights 102 and 104, is also chosen so that the same volume of air has the time to pass through the passage 106, to rejoin the blowing chamber 122 by passing successively through the exhaust chamber 124 and the transfer pipe 126, and to pass through the passage 106 once again, in less time than the duration of the presence of the individual 108 in the detection gate 100.

In a particular embodiment, the depth of the detection gate is around 80 cm.

Naturally, if because of certain constraints it is not possible for the same volume of air to pass through the passage 106 twice during the time taken by the same individual 108 to pass through it, it is possible to provide for the detection gate 100 to comprise a holding device that prevents the individual 108 leaving the detection gate 100 for the time necessary.

The holding device may for example be a door that is placed at the exit from the detection gate 100 and remains closed for the time taken by the same volume of air to pass through the passage 106 twice.

The holding device may for example be a light or audible signal that indicates to the individual whether or not he may leave the detection gate 100.

The fact that the same volume of air passes through the passage 106 twice while best channelling the air flow 114 in the passage 106 theoretically doubles the concentration of molecules of substances to be detected.

The lateral movement of the air flow (114) with respect to the individual 108 makes it possible to best surround the individual 108 while covering the areas ranging from the feet to the head with the same efficacy and thus to recover the molecules of substances to be detected to the maximum extent over all the areas of the body of the individual 108. In addition, it optimises the movement from one side of the individual 108 to the other and makes it possible to cover him entirely, unlike an air flow going from bottom to top.

In the case where the air that is circulating in the detection gate 100 must be purged, for example after a positive detection of a substance, the transfer pipe 126 has a discharge flap 138 that is able to move between a closed position (continuous line) and an open position (broken line). The closed position corresponds to the normal operating position, that is to say when the air is circulating in closed circuit. The open position corresponds to the position in which the air that is circulating in the transfer pipe 126 is discharged. For this purpose, the discharge flap 134 emerges in a flue 140 that optionally comprises an extraction device.

In order to prevent any propagation of pathogenic germs between two individuals 108, a sterilisation device 142, for example of the UV generator type, may for example be installed in the detection gate 100. The sterilisation device 142 is arranged so as to sterilise the air flow circulating between the exhaust means 114 and the blowing means 110 and, in particular, is placed in the transfer pipe 126. This technique has no effect on the molecules of the substances to be detected.

In the embodiment of the invention presented in FIG. 1, the detection device 120 constitutes a detection device based on infrared spectrometry.

The detection device 120 comprises an emitter 144 of the infrared emitter type, a sensor 146, an analyser 148, a first mirror 150 and a second mirror 152. The emitter 144 is arranged opposite a first window produced in the second mirror 152 and the sensor 146 is arranged opposite a second window produced in the second mirror 152.

The emitter 144 emits a light beam 154 that passes through the first window and is reflected on the first mirror 150. After multiple reflections between the two mirrors 150 and 152, the light beam 154 passes through the second window and is picked up by the sensor 146.

The information received by the sensor 146 is transmitted to the analyser 148, which analyses whether, for certain frequencies, the power of the light signal has weakened, thus characterising the presence of particular molecules in the air. If these frequencies represent a substance to be detected, the analyser 148 transmits an alert signal to a suitable alarm device.

The form of the walls channelling the air flow 114, 128, 130 is such that aerodynamic disturbances are minimised. The location and power of the blowing means 110 and of the exhaust means 118 is such that the air flow 114 in the passage 106 remains confined inside the detection gate 100 to the maximum extent and the external air remains outside the detection gate 100 to the maximum extent.

In order to prevent particles sticking on the walls of the detection gate 100, the walls are covered with an anti-adherent coating.

Figure 2:
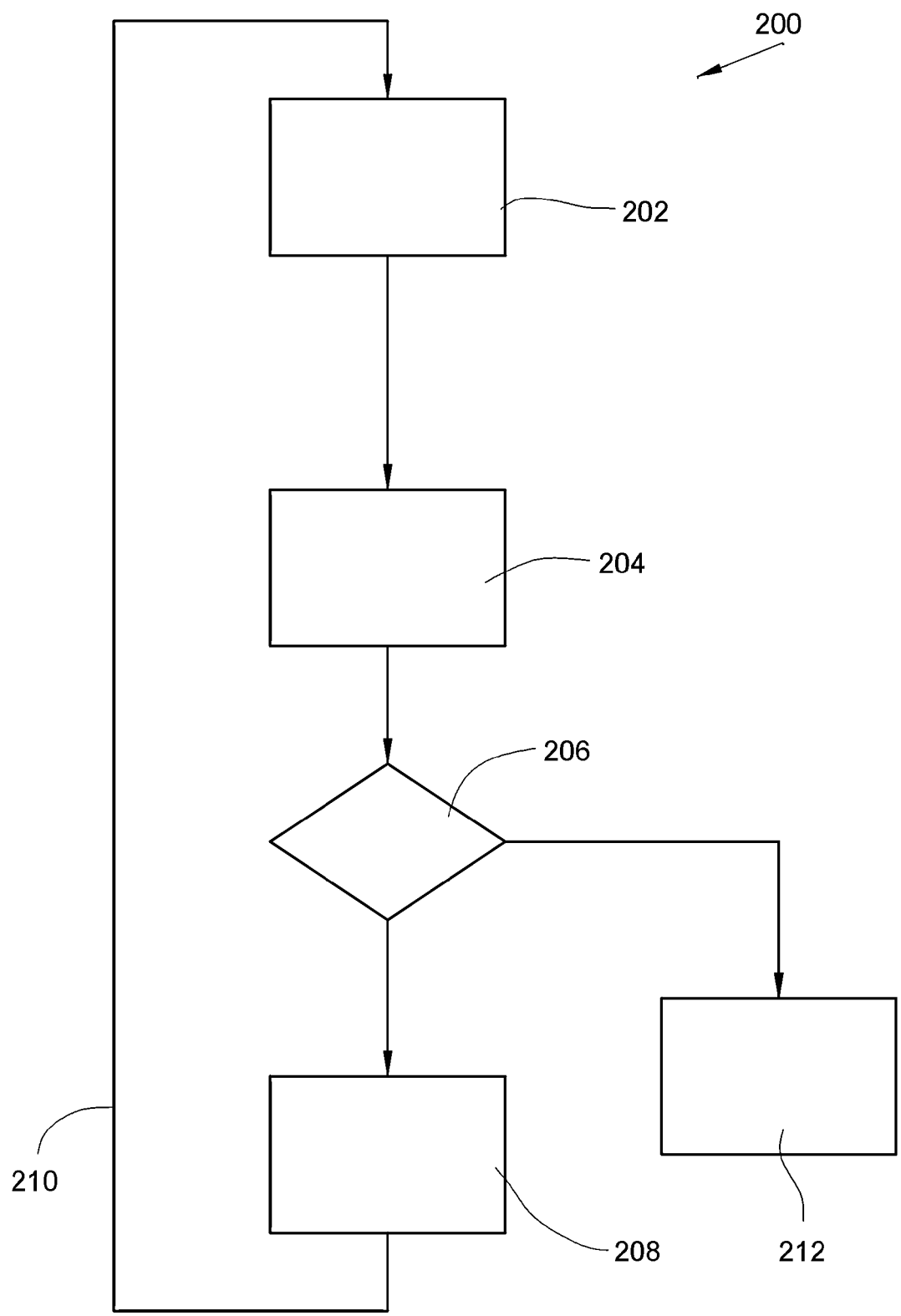
FIG. 2 shows a flow diagram of a detection method according to the invention.

FIG. 2 shows a method of detecting substances carried by the said individual 108 where the said object is implemented by means of the detection gate 100. The detection method 200 comprises:
- a blowing step 202 during which a volume of air from the chamber 122 is blown by the blowing means 110 towards the exhaust means 118,
- an exhaust step 204 during which the said volume of air thus blown is exhausted by the exhaust means 118 in the exhaust chamber 124,
- a detection step 206 during which the detection device detects whether at least one of the said substances is present in the said volume of air thus blown,
- a transfer step 208 during which the air in the exhaust chamber 124 is transferred to the blowing chamber 122 through the transfer pipe 126, and
- a step 210 of looping back onto the blowing step.

The blowing means 110 and the exhaust means 118 are adapted so that the same volume of air has the time to perform the blowing step 202 and the exhaust step 204 twice before the said individual 108 or the said object passes through the said passage 106.

Thus the detection step 206 takes place over a volume of air in which the concentration of substances to be detected is increased.

The blowing step 202, the exhaust step 204, the detection step 206 and the transfer step 208 take place continuously, that is to say the air is continuously in movement.

If during the detection step 206 a positive detection of one of the substances occurs, the process continues with an alert step 212 during which information representing the positive detection is sent to the responsible persons.

When the detection gate 100 comprises the sterilisation device 142, the detection method 200 comprises a sterilisation step between the detection step 206 and the blowing step 202.

When the detection gate 100 comprises the holding device, the detection method 200 comprises a holding step during which the holding device prevents the individual 108 from leaving the detection gate 100.

Naturally, the present invention is not limited to the examples and embodiments described and depicted but is capable of numerous variants accessible to persons skilled in the art.

For example, the invention was more particularly described in the case where the same volume of air passes through the passage 106 twice, but applies in the same way in the case where it is preferred for the same volume of air to pass through the passage 106 more than twice.

The invention claimed is:

1. Detection gate intended to detect substances carried by an individual or an object, the detection gate comprising:
    two lateral uprights facing each other and defining there between them a passage for said individual or said object,
    a blowing chamber realized in one of the lateral uprights, emerging in the passage through only one first ventilated wall through which air in the blowing chamber is blown and comprising blowing means;
    an exhaust chamber realized in the other lateral upright, emerging in the passage through only one second ventilated wall through which the air in the passage is sucked and comprising exhaust means able to suck in the air through said second ventilated wall, the second ventilated wall facing the first ventilated wall,
    a detection device disposed downstream from the passage and able to detect the presence of said substances in the air thus blown,
    a transfer pipe emerging through a first end in the blowing chamber and through a second end in the exhaust chamber,
    the blowing means being adapted to blow the air contained in said blowing chamber through said first ventilated wall directly towards said second ventilated wall and then through the transfer pipe,
    the blowing means and the exhaust means being such that a same volume of unfiltered air is recirculated across the passage at least twice before said individual or said object passes through said passage; and the transfer pipe has a discharge flap configured to move from a closed position to an open position after a detection of a substance by the detection device.

2. Detection gate according to claim 1, wherein the blowing means comprise a plurality of fans distributed over a height of the one upright.

3. Detection gate according to claim 2, wherein at least one of the fans is placed opposite an area where the feet of the individual pass.

4. Detection gate according to claim 1, further comprising a sterilization device intended to sterilize the air flow circulating between the exhaust means and the blowing means.

5. Detection gate according to claim 1, further comprising a holding device intended to prevent the individual leaving said detection gate.

6. Method for detecting substances carried by an individual or an object, and implemented by means of a detection gate according to claim 1, said detection method comprising:
- a blowing step during which a volume of air in a blowing chamber is blown by blowing means towards the exhaust means,
- an exhaust step during which said volume of air thus blown is exhausted by the exhaust means in an exhaust chamber,
- a detection step during which a detection device detects whether at least one of the substances is present in said volume of air thus blown,
- a purging step during which a discharge flap moves from a closed position to an open position after a detection of a substance by the detection device,
- a transfer step during which the air in the exhaust chamber is transferred to the blowing chamber through the transfer pipe, and
- a step of looping back onto the blowing step, wherein the blowing means and the exhaust means are such that the same volume of unfiltered, non-decontaminated air makes the blowing step and exhaust step twice before said individual or said object passes through said passage.

7. Detection method according to claim 6, wherein, when the detection gate comprises a sterilization device, the detection method comprises a sterilization step between the detection step and the blowing step.

* * * * *